United States Patent
Vestal

(10) Patent No.: US 11,105,797 B2
(45) Date of Patent: Aug. 31, 2021

(54) LIGAND BINDING ASSAYS USING MALDI-TOF MASS SPECTROMETRY

(71) Applicant: Virgin Instruments Corporation, Marlborough, MA (US)

(72) Inventor: Marvin L. Vestal, Framingham, MA (US)

(73) Assignee: Virgin Instruments Corporation, Marlborough, MA (US)

( * ) Notice: Subject to any disclaimer, the term of this patent is extended or adjusted under 35 U.S.C. 154(b) by 513 days.

(21) Appl. No.: 15/861,265

(22) Filed: Jan. 3, 2018

(65) Prior Publication Data

US 2018/0188241 A1    Jul. 5, 2018

Related U.S. Application Data

(60) Provisional application No. 62/442,512, filed on Jan. 5, 2017.

(51) Int. Cl.
*G01N 33/53*     (2006.01)
*G01N 33/68*     (2006.01)
*G01N 33/84*     (2006.01)

(52) U.S. Cl.
CPC ..... *G01N 33/5302* (2013.01); *G01N 33/6848* (2013.01); *G01N 33/6851* (2013.01);
(Continued)

(58) Field of Classification Search
CPC ........... G01N 33/5302; G01N 33/6893; G01N 33/6848; G01N 33/84; G01N 33/6851;
(Continued)

(56) References Cited

U.S. PATENT DOCUMENTS

| 7,282,707 | B1 | 10/2007 | Zanon |
| 9,513,285 | B2 | 12/2016 | Lim et al. |

(Continued)

FOREIGN PATENT DOCUMENTS

| WO | 2012109460 A1 | 8/2012 |
| WO | 2014/176435 A2 | 10/2014 |

OTHER PUBLICATIONS

Zhou et al. (Scientific Reports May 2016 (pp. 1-8) (Year: 2016).*

(Continued)

*Primary Examiner* — Sally A Merkling
(74) *Attorney, Agent, or Firm* — Rauschenbach Patent Law Group, LLC; Kurt Rauschenbach

(57) ABSTRACT

An apparatus for ligand binding assays includes an incubator that incubates a plurality of beads with a sample of interest wherein each of the plurality of beads comprises a tag of predetermined mass and a bait molecule. A washer washes the incubated beads so that weakly bound molecules are removed while strongly bound molecules are retained. A sample plate loader loads the washed beads into the sample plate such that respective ones of the plurality of beads are loaded into respective ones of the plurality of well. A sprayer deposits matrix assisted laser desorption ionization (MALDI) matrix material on the surface of the sample plate so that each of the plurality of beads is exposed to MALDI matrix material. A MALDI-TOF mass spectrometer receives the sample plate and performs mass spectrometry on samples in the plurality of wells. A computer executes an algorithm that analyzes the mass spectra.

15 Claims, 6 Drawing Sheets

(52) U.S. Cl.
CPC ......... *G01N 33/6893* (2013.01); *G01N 33/84* (2013.01); *G01N 2560/00* (2013.01)

(58) Field of Classification Search
CPC .. G01N 2560/00; G01N 33/543; G01N 33/58; G01N 33/6845
See application file for complete search history.

(56) References Cited

U.S. PATENT DOCUMENTS

| | | | |
|---|---|---|---|
| 2004/0018515 A1* | 1/2004 | Diener | B82Y 30/00 435/6.16 |
| 2004/0023217 A1 | 2/2004 | Gut et al. | |
| 2006/0003366 A1 | 1/2006 | DiCesare | |
| 2008/0090295 A1 | 4/2008 | Feuerstein et al. | |
| 2012/0202709 A1 | 8/2012 | Bergo | |
| 2014/0274771 A1 | 9/2014 | Elizazu et al. | |
| 2016/0008785 A1 | 1/2016 | Bergo | |
| 2016/0225596 A1 | 8/2016 | Hayden et al. | |

OTHER PUBLICATIONS

Huiyan Li et al, "Bead-Extractor Assisted Ready-to-Use Reagent System (BEARS) for Immunoprecipitation Coupled to MALDI-MS", Mar. 3 2017, 6 Pages, ACS Publications, American Chemical Society, Washington, DC, United States of America.

"European Search Report" for EP Patent Application No. 18736271.0, dated Jul. 16, 2020, 8 pages, European Patent Office, Munich, Germany.

Ying Zhou, et al., Proteome-wide Drug Screening Using Mass Spectrometric Imaging of Bead-Arrays, Scientific Reports, May 19, 2016, vol. 6, No. 1, pp. 1-8, XP055511841, DOI: 10.1038/srep26125, www.nature.com/scientificreports.

Scientific Reports, 2016, vol. 6, Article No. 26125 (internal pp. 1-8). Notification Concerning Transmittal of International Preliminary Report on Patentability (Chapter I of the Patent Cooperation Treaty) for International Patent Application No. PCT/US2018/012199, dated Jul. 18, 2019, 11 Pages, The International Bureau of WIPO, Geneva, Switzerland.

Zhou, Ying et al., "Proteome-wide drug screening using mass spectrometric imaging of bead-arrays" Scientific Reports, 2016, vol. 6, Article No. 26125.

"Notification of Transmittal of the International Search Report and the Written Opinion of the International Searching Authority, of the Declaration", For International Patent application No. PCT/US2018/012199, dated Apr. 30, 2018, 14 Pages, Korean Intellectual Property Office ISA/KR, Daejeon, Republic of Korea.

* cited by examiner

| NUMBER | DESCRIPTION |
|---|---|
| 21329 | EZ-LINK NHS-PEG$_4$-BIOTIN, NO-WEIGHT FORMAT, 8x2mg MICROTUBES |
| 21330 | EZ-LINK NHS-PEG$_4$-BIOTIN, 25mg |
| 21362 | EZ-LINK NHS-PEG$_4$-BIOTIN, 50mg |
| 21363 | EZ-LINK NHS-PEG$_4$-BIOTIN, 1g |

MOLECULAR WEIGHT: 588367
SPACER ARM: 29Å
NET MASS ADDITION: 473.22
STORAGE: UPON RECEIPT STORE AT -20°C PROTECTED FROM MOISTURE.

LIGAND BINDING ASSAYS USING MALDI-TOF MASS SPECTROMETRY

CROSS REFERENCE TO RELATED APPLICATION

The present application is non-provisional application of U.S. Provisional Patent Application Ser. No. 62/442,512, entitled "Ligand Binding Assays Using MALDI-TOF Mass Spectrometry" filed on Jan. 5, 2017. The entire contents of U.S. Provisional Patent Application Ser. No. 62/442,512 are herein incorporated by reference.

The section headings used herein are for organizational purposes only and should not to be construed as limiting the subject matter described in the present application in any way.

INTRODUCTION

Major research efforts are focusing on characterizing the millions of interactions of the human proteome with other molecules. These include proteins, nucleic acids, lipids, and metabolites. Immunoassays are very important tools that are used to perform this work. Factors such as: (1) the rising incidences of chronic and infectious diseases; (2) the rapidly expanding biotechnology and pharmaceutical industries; (3) the extensive use of immunoassays in oncology because of its cost-effectiveness and rapid action; (4) and the growing geriatric population are expected to propel the growth of the immunoassay market in the coming years. See, for example, Genetic and Engineering & Biotechnology News, Sep. 15, 2016, p. 12. It is, however, highly desirable to have an alternative to the widely used Enzyme-Linked Immunosorbent Assays (ELISA) that is significantly faster, more sensitive, and less expensive.

Ligand binding assays have been used to measure of the interactions that occur between two molecules, such as protein-bindings, as well as the degree of affinity for which the reactants bind together. More specifically, ligand binding assays are used to test for the presence of target molecules in a sample that is known to bind to the receptor. Various detection methods have been used to determine the presence and extent of the ligand-receptor complexes formed. Known methods include electrochemical detection through various fluorescence detection methods.

BRIEF DESCRIPTION OF THE DRAWINGS

The present teaching, in accordance with preferred and exemplary embodiments, together with further advantages thereof, is more particularly described in the following detailed description, taken in conjunction with the accompanying drawings. The skilled person in the art will understand that the drawings, described below, are for illustration purposes only. The drawings are not necessarily to scale, emphasis instead generally being placed upon illustrating principles of the teaching. The drawings are not intended to limit the scope of the Applicant's teaching in any way.

DESCRIPTION OF VARIOUS EMBODIMENTS

Figure 1:
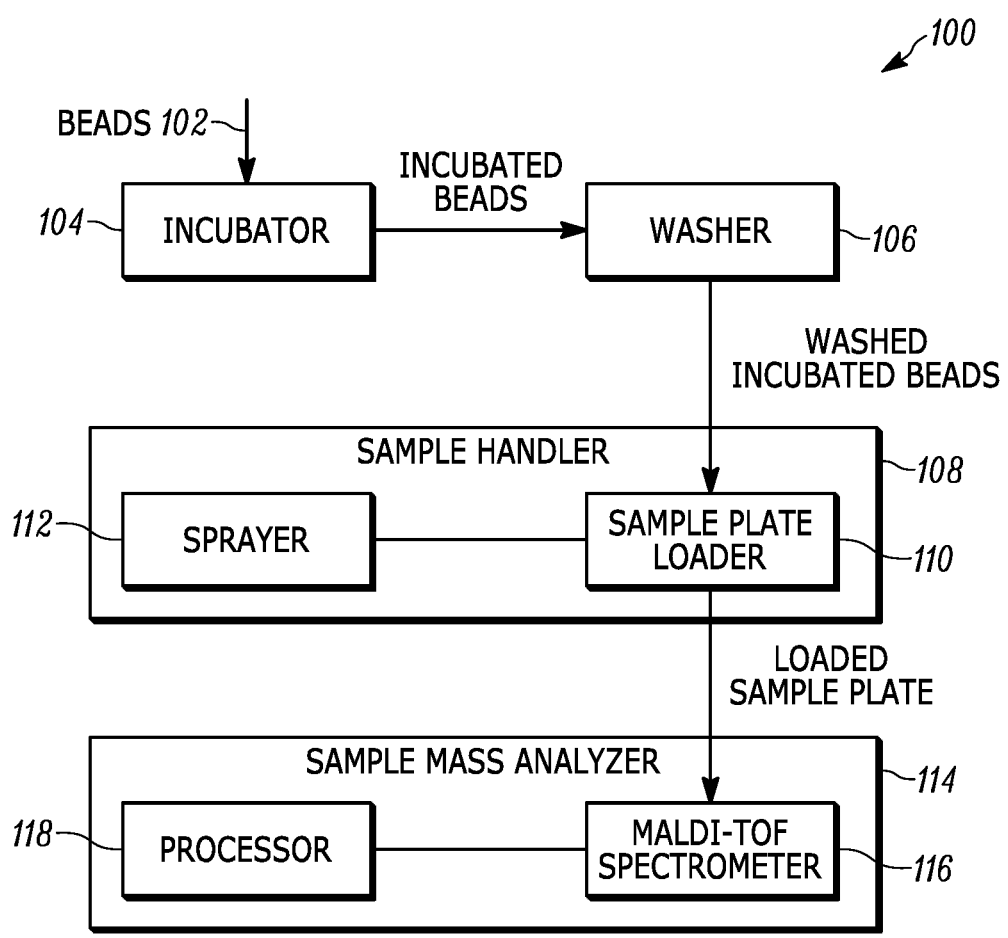
FIG. 1 illustrates a block diagram of an embodiment of a ligand binding assay apparatus according to the present teaching that produces and analyzes ligand binding assays.

The present teaching will now be described in more detail with reference to exemplary embodiments thereof as shown in the accompanying drawings. While the present teachings are described in conjunction with various embodiments and examples, it is not intended that the present teachings be limited to such embodiments. On the contrary, the present teachings encompass various alternatives, modifications and equivalents, as will be appreciated by those of skill in the art. Those of ordinary skill in the art having access to the teaching herein will recognize additional implementations, modifications, and embodiments, as well as other fields of use, which are within the scope of the present disclosure as described herein.

Reference in the specification to "one embodiment" or "an embodiment" means that a particular feature, structure, or characteristic described in connection with the embodiment is included in at least one embodiment of the teaching. The appearances of the phrase "in one embodiment" in various places in the specification are not necessarily all referring to the same embodiment.

It should be understood that the individual steps of the methods of the present teachings can be performed in any order and/or simultaneously as long as the teaching remains operable. Furthermore, it should be understood that the apparatus and methods of the present teachings can include any number or all of the described embodiments as long as the teaching remains operable.

One aspect of the present teaching relates to providing a highly multiplexed Mass Spectrometric ImmunoAssay (MSIA) that can be used as an alternative to widely used Enzyme-Linked Immunosorbent Assays (ELISA). In particular, the apparatus and method of the present teaching can be used to perform multiplexed detection and characterization of single cells. Using the highly multiplexed Mass Spectrometric ImmunoAssay of the present teaching can provide much faster results with higher sensitivity and higher dynamic range that are less expensive to produce compared with the widely used Enzyme-Linked Immunosorbent Assays. Apparatus of the present teaching can be fully automated to achieve very high throughput at relatively low cost. One feature of these apparatus is that they can be label-free since fluorescent tags are not required.

One application of the method and apparatus of the present teaching relates to screening of a human protein library to discover new autoimmune and tumor antigens in patient sera for clinical diagnostics and immunotherapy. Another application of the method and apparatus of the present teaching relates to screening of a synthetic combinatorial library against specific protein targets to discover new drugs. Another application of the method and apparatus of the present teaching relates to developing drug compounds with high efficacy and minimal side-effects to assist in new drug discoveries.

More specifically, some embodiments of the apparatus and method for ligand binding assays according to the present teaching use beads prepared with a tag of predetermined mass and a bait molecule attached. In one embodiment, the beads comprise Streptavidin Sepharose® High Performance beads, which are commercially available from GE Healthcare Life Sciences. One type of suitable bead is GE Healthcare Life Sciences Product Code: 17-5113-01. These Streptavidin Sepharose® beads are nominally 34 µm in diameter. The mass tag molecules and bait molecules are biotinylated and are bound to the beads by the streptavidin-biotin interaction. Biotinylation is a process of covalently attaching biotin to a protein, nucleic acid or other molecule. Biotinylation is both a rapid and a specific process. Furthermore, biotinylation is performed without a significant perturbation to the natural function of the molecule due to the small size of biotin (MW=244.3 Da).

FIG. 1 illustrates a block diagram 100 of an embodiment of a ligand binding assay apparatus according to the present teaching that produces and analyzes ligand binding assays. The ligand binding assay apparatus 100 accepts beads 102 into an incubator 104 with a tag of predetermined mass and a bait molecule attached. In one embodiment, the beads 102 comprise Streptavidin Sepharose High Performance beads. In this embodiment, the mass tag molecules and bait molecules are biotinylated and are bound to the beads 102 by the streptavidin-biotin interaction. The beads 102 are loaded into an incubator 104. The incubator 104 incubates the bait molecule with samples of interest so that the bait molecules strongly bind to target molecules contained in the sample.

The ligand binding assay apparatus 100 further comprises a washer 106 that washes the incubated beads 102. The washer 106 dispenses washing fluid on the beads and agitates the incubated beads 102 in the washing fluid. In some embodiments, the properties of the washing solution are chosen so that weakly bound molecules are cleaved from the beads 102 and strongly bound molecules remain attached to the beads 102.

The washed beads 102 are then transferred to a sample handler 108 that includes a sample plate loader 110 and matrix material applicator 112, such as a sprayer. One skilled in the art will appreciate that numerous types of matrix material applicators can be used to spray and/or directly apply matrix materials. In some embodiments, the incubated and washed beads are positioned on a sample plate suitable for MALDI-TOF analysis. In one embodiment the surface of the sample plate comprises a plurality of microwells where the dimensions of the microwells are chosen so that only one bead can be contained within any given microwell. That is, the number of beads applied to the microwell sample plate is not greater than the number of microwells in each region of the microwell sample plate. Microwell sample plates are described in more detail in connection with FIGS. 3A, 3B, 4A and 4B. In one embodiment, both the diameter and the depth of the microwells of the microtiter sample plate are on order of about 40 µm.

The sample plate loader 110 applies a suspension of incubated and washed beads 102 in appropriate liquid to each desired region of the sample plate where the number of beads 102 applied is not greater than the number of beads that can be spread in a monolayer in the desired region of the sample plate. In some embodiments comprising microwell plates, the number of beads is not greater than the number of microwells in that region of the microwell sample plate.

In one embodiment, the sample plate is divided into regions with a cover having apertures that separate the sample plate into predetermined portions with a gasket that prevents liquid from flowing between separate regions. The sample plate loader 110 then agitates the sample plate with a vibrator causing beads to spread out in a monolayer on the sample plate. Also, in some embodiments comprising microwell plates, the sample plate loader 110 then agitates the sample plate with a vibrator causing each bead to settle into a microwell and eventually dry.

The sample handler 108 also includes a matrix material applicator 112 for depositing MALDI matrix on the surface of the sample plate. In some apparatus, the matrix material applicator 112 can included a sprayer or equivalent type of apparatus that produces small droplets of fluid with MALDI matrix material. One suitable sprayer for spraying these very small droplets is the HTX TM-Sprayer, which is commercially available from HTX Technologies in Chapel Hill, N.C. The matrix solution sprayed on the microtiter sample plate is allowed to dry. The drying process causes rupture of the streptavidin-biotin bonds and rupture of the non-covalent bonds between bait molecules and the strongly bound target molecules. The rupture results in the released molecules being incorporated into matrix crystals.

The sample plate handler 108 also includes a transfer mechanism that transfers the incubated and washed beads 102 in the sample plate to the sample mass analyzer 114. The sample mass analyzer 114 comprises a mass spectrometer 116 such as a Time-of-Flight (TOF) mass spectrometer like the matrix-assisted laser desorption/ionization (MALDI) TOF mass spectrometers manufactured by Virgin Instruments Corporation, the assignee of the present application. The operation of MALDI TOF mass spectrometers is well known in the art. A laser ionization source generates a laser beam that scans over the surface of the sample plate producing and recording a mass spectrum from each location on the multi-well sample plate.

One feature of the present teaching is that a translation stage can be used to move the sample plate in two dimensions to scan the laser in the MALDI-TOF mass spectrometer 116 to ionize samples over the entire two-dimensional surface of the sample plate so that the MALDI-TOF mass spectrometer 116 can produce and record a mass spectrum from each location on the plate.

A processor 118, such as a computer, interfacing with the MALDI TOF mass spectrometer 116 executes an algorithm using the spectra data generated by the MALDI TOF mass spectrometer 116 to detect the predetermined mass to produce a mass spectrum of the molecules that were originally bound to the beads by the streptavidin-biotin bonds. In one method according to the present teaching, the mass spectra in which the predetermined mass of the mass tag is detected are summed together to produce a mass spectrum of the molecules that were originally bound to the beads by the streptavidin-biotin bonds and the target molecules that were bound to the bait molecules. The processor then uses the mass spectrum to produce a ligand binding assay.

Figure 2:
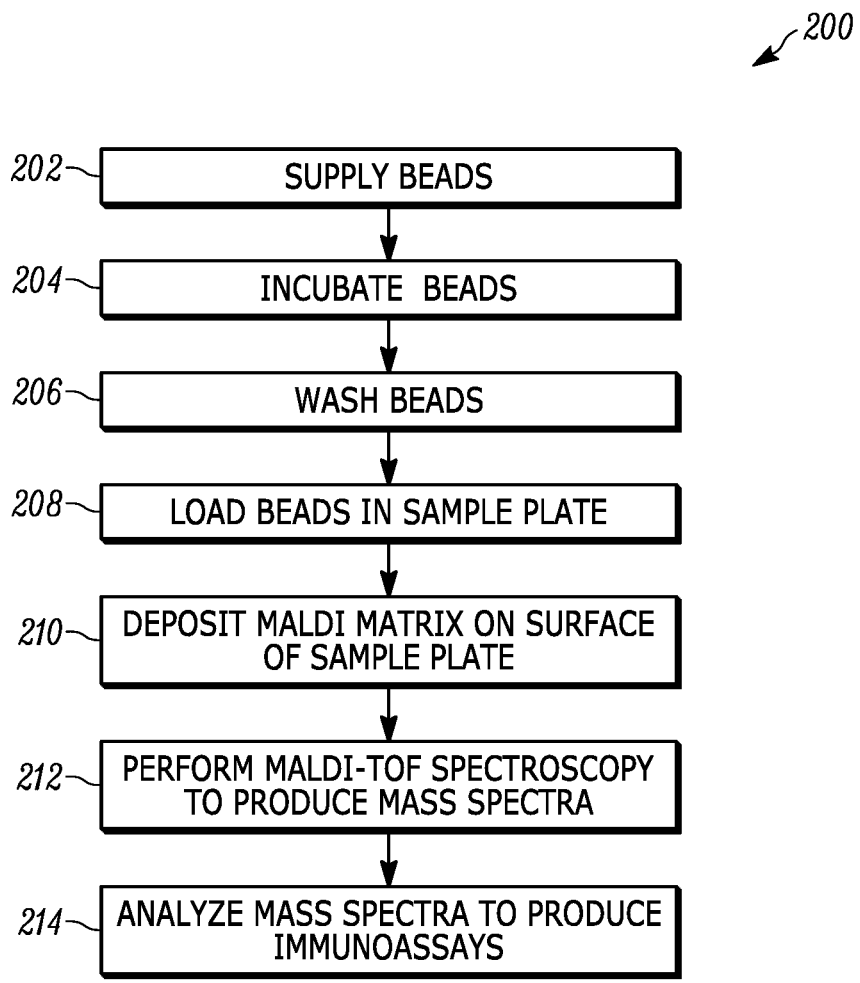
FIG. 2 illustrates a flow diagram of an embodiment of a method of generating ligand binding assays by MALDI-TOF mass spectrometry according to the present teaching.

FIG. 2 illustrates a flow diagram of a method 200 of generating ligand binding assays by MALDI-TOF mass spectrometry 100 according to the present teaching. Referring to both the block diagram of the embodiment of a ligand binding assay apparatus 100 described in connection with FIG. 1 and the flow diagram of the method 200, in step one 202, the beads 102 are supplied. In some embodiments, the beads include a tag of predetermined mass and a bait molecule attached. In one specific embodiment, the beads 102 comprise Streptavidin Sepharose High Performance beads which are commercially available from GE Healthcare Life Sciences. In some embodiments, the mass tag molecules and bait molecules are biotinylated and are bound to the beads by the streptavidin-biotin interaction. In another specific embodiment, ligand-binding assays are produced from biological samples, where small aliquots of affinity beads are added to a biological sample. For example, the biological sample can be human serum, diluted as appropriate.

Step two 204 of the method 200 includes incubating beads 102 with samples of interest. In the incubation step two 204, the bait molecule strongly binds to a molecule contained in the sample. In one embodiment, incubating beads 102 with samples of interest comprises mixing a sample and the beads 102 in predetermined relative liquid volumes in a well in a microtiter plate. The mixture of a sample and beads 102 is agitated to bring beads 102 in contact with sample molecules. Then, after a predetermined time, the beads 102 are allowed to settle in the bottom of the well and supernatant liquid is withdrawn. In one specific embodiment, the beads 102 are incubated for 30 min under agitation to allow for analyte binding.

Step three 206 of the method 200 includes washing the incubated beads 102. In one specific embodiment, the beads 102 are collected by centrifugation in a microcentrifuge tube and washed multiple times in 20 mM Tris pH 7.3, 5 mM EDTA, 1 M NaCl and then washed multiple times in the same Tris pH 7.3 buffer in the absence of salt. After the final wash, the remaining beads are re-suspended in a minimum volume of buffer, also referred to as a carrier solvent.

During the washing procedure, weakly bound molecules are removed while strongly bound molecules are retained. In one method according to the present teaching, step three 206 includes adding a washing solution to the wells in the microtiter plate and then agitating the microtiter plate so that the beads interact with the washing solution. In some methods according to the present teaching, the washing solution is chosen such that the washing step causes weakly bound molecules to cleave from the beads while strongly bound molecules remain attached to the beads.

Step four 208 of the method 200 includes loading the incubated and washed beads 102 in a sample plate. In some methods, the sample plate comprises a microwell sample plate with a plurality of wells where each well has dimensions chosen so that only one bead is contained within the well. In one specific embodiment of the microwell sample plate, both the diameter of the wells and their depth is on order of about 40 µm. In some methods, step four 208 includes transferring incubated beads to the surface of the sample plate so that each bead 102 is contained in a well in a predetermined region of the sample plate. In some methods according to the present teaching, the step of loading the incubated and washed beads 102 comprises spreading the re-suspended remaining beads 102 in the carrier solvent over a well-defined area of the sample plate and drying the beads 102.

In one specific embodiment of the sample plate, the sample plate is divided into regions by a cover with apertures that separate the plate into predetermined portions with a gasket that prevents liquid from flowing between separate regions. With these sample plates, a suspension of beads 102 in appropriate liquid is applied to each region with the number of beads 102 applied being limited to the number of microwells in that region of the sample plate. The plate is then agitated causing each bead 102 to settle into a microwell of the sample plate. The plate is then allowed to dry.

Step five 210 of the method 200 includes depositing a MALDI matrix on the surface of the sample plate. In some methods of depositing a MALDI matrix, the cover and gasket are removed from the sample plate and a solution of MALDI matrix is applied onto the surface of the sample plate with a spraying apparatus. In some methods, the spraying apparatus produces very small droplets. After the MALDI matrix solution is sprayed on the surface of the sample plate, the matrix solution on the sample plate is then allowed to dry. The drying process causes rupture of the streptavidin-biotin bonds and rupture of the non-covalent bonds between bait molecules and strongly bound target molecules. The rupture causes a release of molecules that are then incorporated into the matrix crystals. The loaded sample plate with the MALDI matrix material applied is installed in a MALDI-TOF mass spectrometer.

In some methods of depositing a MALDI matrix, a solution of MALDI matrix is deposited directly on the surface of each region of the sample plate and allowed to dry. The drying process causes rupture of the streptavidin-biotin bonds and rupture of the non-covalent bonds between bait molecules and strongly bound target molecules. The rupture causes a release of molecules that are then incorporated into the matrix crystals. The cover and gasket are removed from the sample plate, and then the loaded sample plate with the MALDI matrix material applied is installed in a MALDI-TOF mass spectrometer.

Step six 212 of the method 200 includes performing MALDI-TOF mass spectroscopy to produce a mass spectra. MALDI-TOF mass spectroscopy is performed by scanning a laser beam over the surface of the sample plate to produce mass spectra. In some methods, the sample plate is moved to cause the laser beam to scan over the surface of the sample plate producing a mass spectrum from each location or pixel on the sample plate. In some embodiments, a mass spectrum is recorded from each microwell location in the sample plate.

In some methods, the detection limit for MALDI-TOF spectroscopy is not limited by chemical noise. In these embodiments, the detection limit for MALDI-TOF spectroscopy is about 1 femtomole/mm$^2$. The detection limit for MALDI-TOF spectroscopy corresponds to 1.3 attomoles/bead or equivalently 780,000 molecules/bead which is 0.04 pg for PSA. In some measurements, one bead may be sufficient to realize a desired detection limit for MALDI-TOF spectroscopy. In other measurements, multiple beads are used to produce lower detection limits, greater dynamic range, and better coefficient of variation CV, which is the ratio of the standard deviation of the peak intensity to the mean.

Step seven 214 of the method 200 includes analyzing the mass spectra to produce immunoassays. In some methods according to the present teaching, the analyzing the mass spectra comprises executing a computer algorithm that sums the mass spectra obtained for the predetermined mass of a mass tag together to produce a mass spectrum of the molecules that were originally bound to the beads by the streptavidin-biotin bonds and the target molecules that were bound to the bait molecules. In one specific method, a computer algorithm sums all of the mass spectra in which a predetermined mass tag is detected to produce a mass spectrum of the bound target molecules. Each given mass tag detected corresponds to a unique bait molecule. Thus, the mass spectra in which the mass tag is detected also include the mass of captured molecules that are strongly bound to the bait molecule.

Figure 3A:
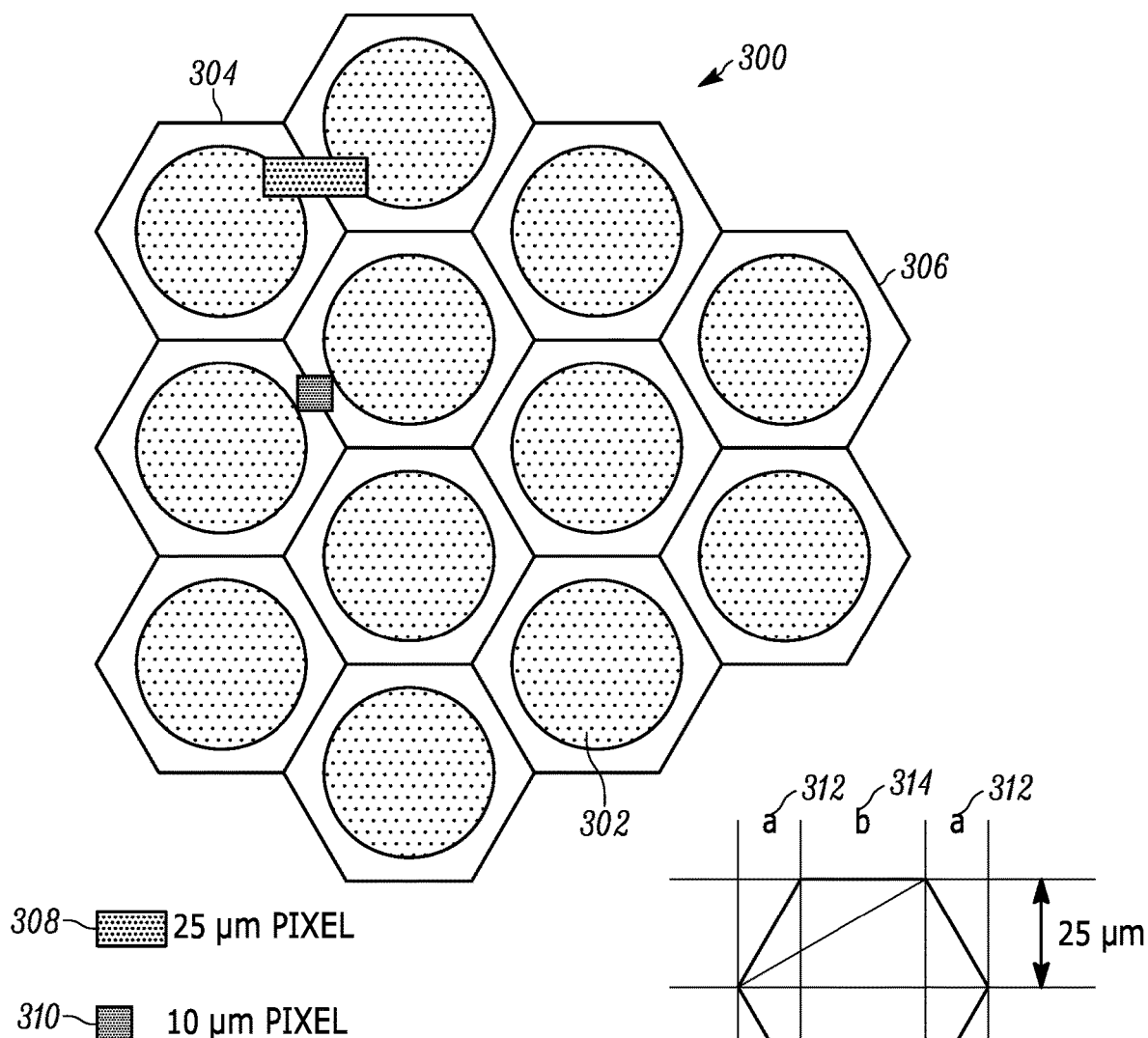
FIG. 3A illustrates a layout of a portion of a microwell sample plate of the ligand binding assay apparatus according to the present teaching.

FIG. 3A illustrates a layout of a portion of a microwell sample plate of the ligand binding assay apparatus according to the present teaching. In the embodiment shown in FIG. 3A, the microwells 302 are 40 μm in diameter and are arranged in a regular hexagonal array 304 with individual hexagons 306 having a 50 μm height. FIG. 3A shows the size of a 25-μm pixel 308 and a 10-μm pixel 310 in relation to the size of an individual hexagon 306 and the regular hexagon array 304. In the example layout 300 shown in FIG. 3A, there are nominally 462 cells/mm$^2$.

Figure 3B:
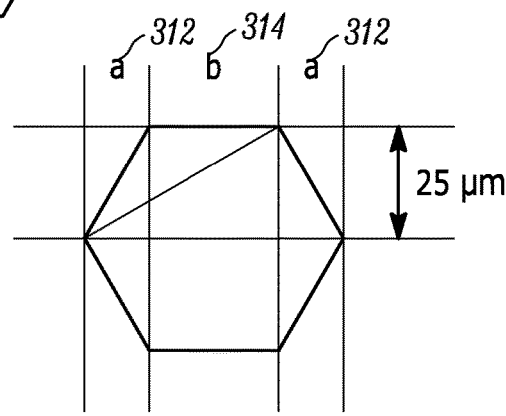
FIG. 3B illustrates a detailed view of one particular hexagon in the hexagonal array shown in FIG. 3A.

FIG. 3B shows a detailed view of one particular hexagon in the hexagonal array 304 shown in FIG. 3A. The hexagon layout has two hexagonal dimensions, a 312 and b 314. In one particular example, the hexagon has a half-height of 25 μm, which corresponds to a=25) tan(30°), and b=50 cos (30°)–a, so that b+2a=57.72 μm.

In some embodiments of the ligand binding assay apparatus according to the present teaching, the laser beam in MALDI-TOF mass spectrometer is rastered over the surface of a microwell plate comprising the layout 300 illustrated in FIG. 3A. In one particular method, the rastering is performed at intervals of 25 μm with a 10-μm diameter laser beam using laser repetition rate of 5 kHz, a scanning speed of 2.5 mm/s, and summing of 50 laser shots per pixel to produce 25 μm long pixels. In this particular method, the total pixels/cell ratio is about 3.5 with about half on the well and half with significant contribution from adjacent wells. Total number of laser shots on each well is 100, with the laser irradiation time per cell equal to about 0.035 s.

In another specific method, the rastering is performed over the surface of microwell plate comprising the layout 300 illustrated in FIG. 3A at intervals of 10 μm with a 10-μm diameter laser beam using laser repetition rate of 5 kHz, scanning speed of 1 mm/s, and summing of 50 laser shots per pixel to produce 10 μm long pixels. In this particular method, the total pixels/cell ratio is about 25 with about 58% on the well having no significant contribution from adjacent wells. Total number of laser shots on the well is 600, and the laser irradiation time per cell is 0.25 seconds.

In another specific method, the rastering is performed over the surface of microwell plate comprising the layout 300 illustrated in FIG. 3A at intervals of 12.5 μm with a 10-μm diameter laser beam using laser repetition rate of 5 kHz, scanning speed of 1.25 mm/s, and summing of 50 laser shots per pixel to produce 12.5 μm long pixels. In this particular method, the total pixels/cell ratio is about 16 with about 58% on the well and with no significant contribution from adjacent wells. Total number of laser shots on each well is 400 with the laser irradiation time equal to 0.16 seconds.

Figure 4A:
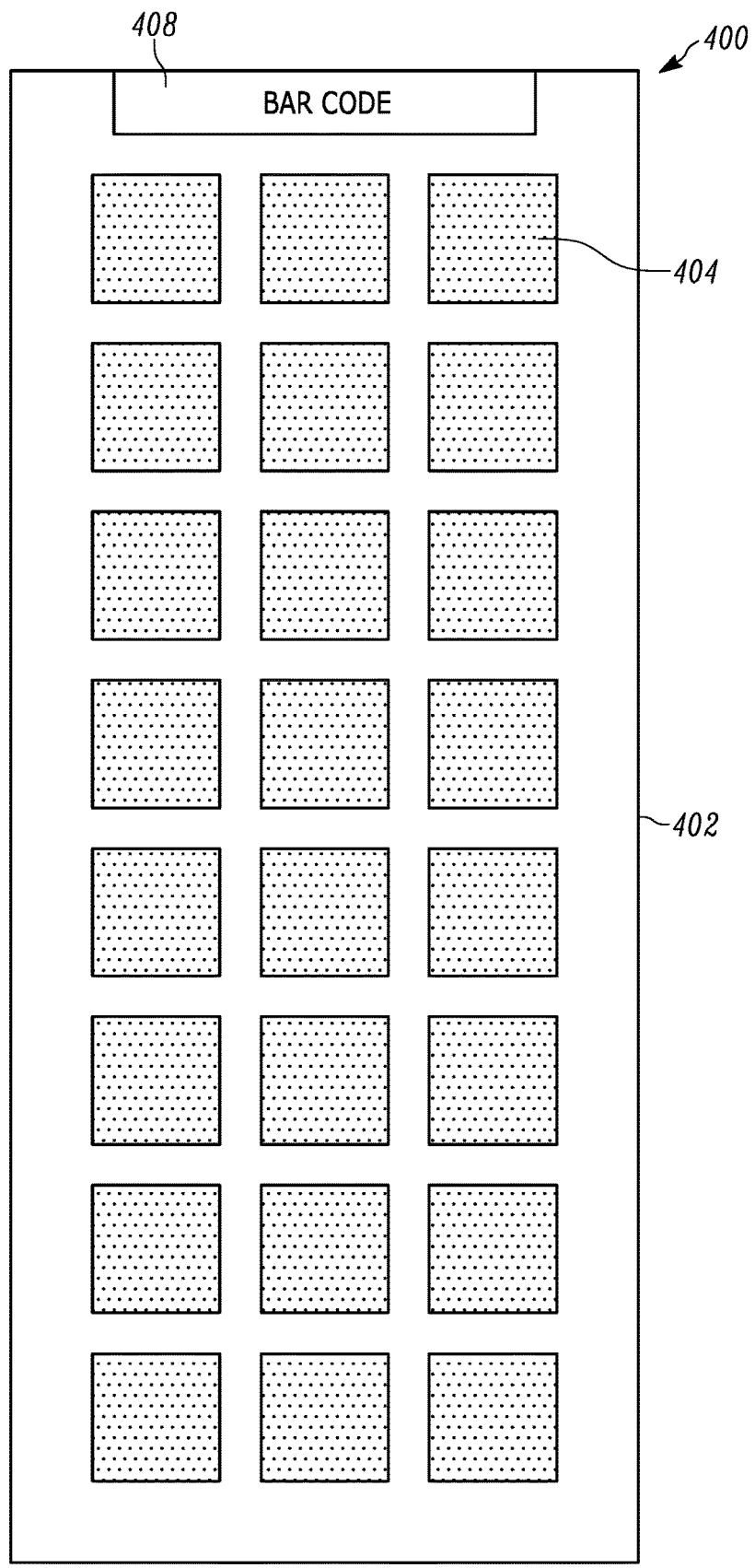
FIG. 4A illustrates a layout of an embodiment of a sample plate with division into regions according to the present teaching.

FIG. 4A illustrates a layout 400 of an embodiment of a microwell sample plate 402 with division into regions according to the present teaching. In one particular plate according to the present teaching, the microwell plate 402 has nominally a 25×75 mm outside dimensions and comprises approximately 866,250 microwells. The microwell plate 402 is separated into regions or spots 404 by masks that are clamped to the plate with a gasket (not shown) that prevents liquid flow between the spots 404. The plate 400 shown in FIG. 4A illustrates a layout 400 comprising twenty-four spots 404 arranged in a 3×8 array. Each spot 404 is 7×7 mm and there is a 1-mm-long space between spots 404. Each spot 404 comprises approximately 22,600 microwells. The twenty-four spots include a total of about 542,400 wells. With a MALDI-TOF processing time of one hour per spot, the MALDI-TOF process completes in 24 hours per sample plate. A bar code 408 is attached to the plate at one end in a region 6×25 mm to identify the plate.

Figure 4B:
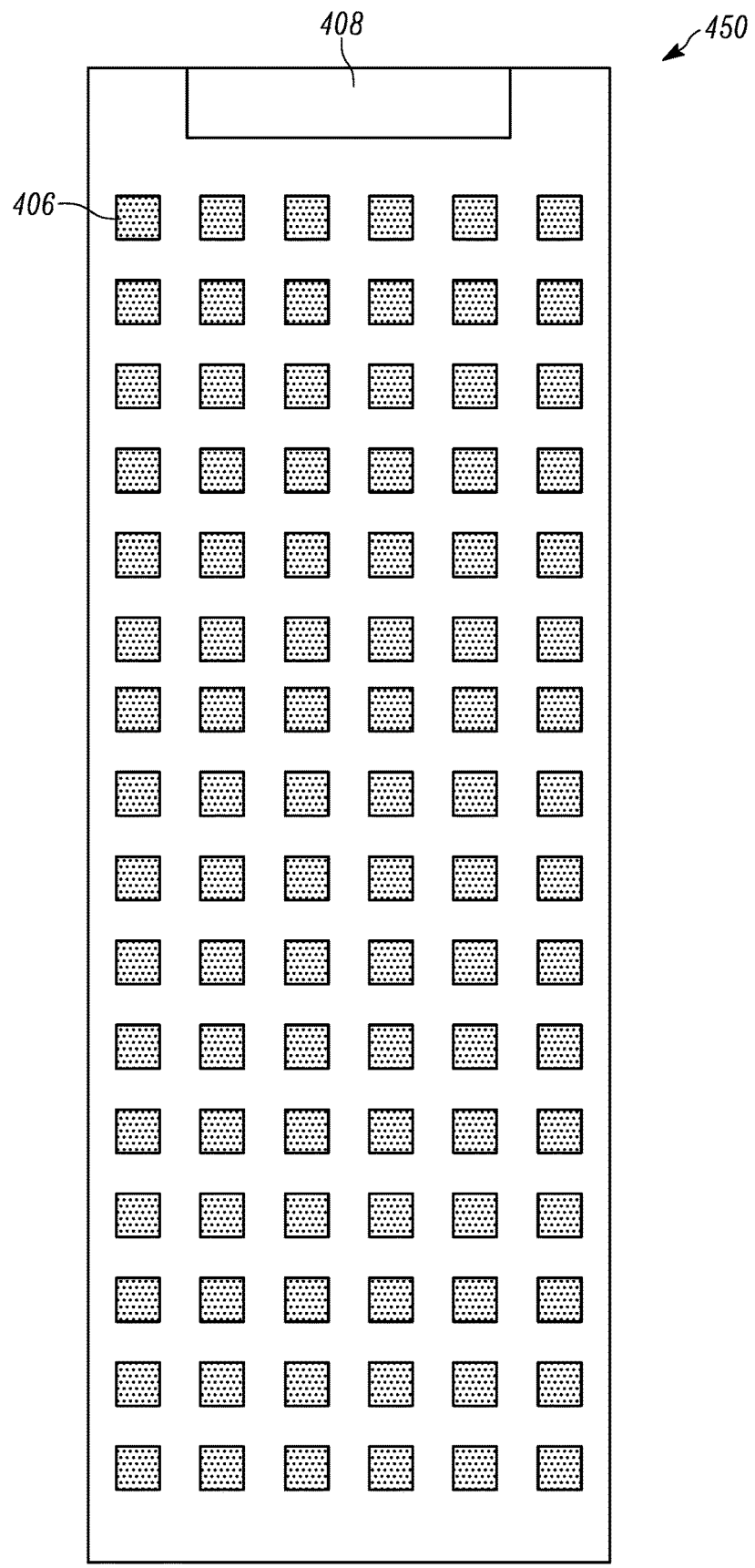
FIG. 4B illustrates a layout of another embodiment of a sample plate with division into regions according to the present teaching.

FIG. 4B illustrates a layout 450 of another embodiment of a microwell sample plate with division into regions according to the present teaching. FIG. 4B illustrates a layout 450 that comprises ninety-six spots 406 arranged in an 8×20 array. Each spot 406 is 3×3 mm and there is a 1-mm-long space between spots 406. Each spot 406 comprises approximately 4100 microwells.

In another particular layout (not shown), the plate comprises three-hundred eighty-four spots arranged in a 12×32 array with each spot being dimensioned 1.5×1.5 mm and with a 0.5-mm-long space between spots. Each spot comprises approximately 1030 microwells. In yet another particular layout (not shown), the plate comprises one-thousand five hundred and thirty-six spots arranged in a 24×64 array with each spot being dimensioned 0.5×0.5 mm and with 0.5 mm space between spots. In this layout, each spot comprises approximately 115 microwells. Those skilled in the art will recognize that any number of spots can be arranged as needed for a particular application.

The methods of the present teaching are particularly well suited to producing a ligand binding assay from biotin. Biotin (MW=244.3 Da), is a vitamin involved in several biological processes. These biological processes include, for example, cell growth and the citric acid cycle that is present, in low quantity, in all living cells. Streptavidin (MW~52K), is a tetrameric protein purified from the bacterium *Streptomyces Avidinii* that is capable of binding 4 biotin molecules with extremely high affinity (Kd=10-14M). Biotin is a relatively small molecule, which is easily bonded to peptides or aptamers with negligible impact on biological activity. Biotin/Streptavidin association occurs rapidly, and is relatively stable with temperature changes, with organic solvents, with many denaturing agents, and is stable across pH range of about 4-9. These features of biotin and streptavidin chemistry make it a particularly useful tool for designing biological assay systems.

Figure 5:
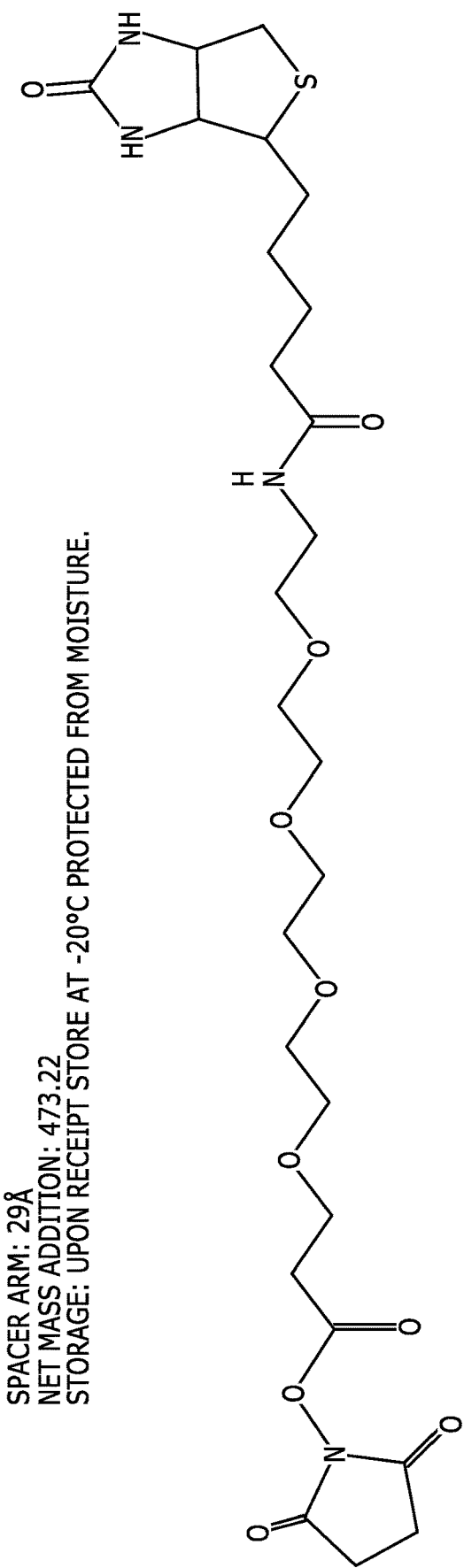
FIG. 5 illustrates a commercially available biotin linker employed to covalently attach biotin to molecules of interest for use in the ligand binding assay method and apparatus of the present teaching.

FIG. 5 illustrates a commercially available biotin linker 500 employed to covalently attach biotin to molecules of interest in an embodiment of the ligand binding assay apparatus and method of the present teaching. As illustrated in FIG. 5, the mass of biotinylated molecule is increased by 473.22 Da by this addition of the biotin. The masses of biotinylated peptides used for mass tags must be sufficiently different to be distinguished by the mass spectrometer. Taking into account the isotopic envelopes, a difference of 2000 ppm is adequate. The total number of theoretically distinguishable peaks, n, is 550 with a mass range, $m_n$-$m_0$, of 800-2400 Da and a resolution of 2000 ppm. This is calculated as follows:

$$m_n = m_0(1+0.002)^n$$

$$n = \log(3)/\log(1.002) = 550.$$

A list of peptides can be generated with a mass range, $m_n$-$m_0$, of 800-2400 Da and a resolution of 2000 ppm to approach this theoretical limit. These suitable peptides are chosen with biotinylated N-terminus and C-terminal arginine (R) and up to 12 other amino acid in order to obtain a relative uniform response factors with MALDI-TOF MS.

One feature of the ligand-binding assay apparatus and method of the present teaching is the ability to utilize a number of known and commercially available beads. For example, in some embodiments, purified Streptavidin Sepharose beads, which are commercially available through GE Healthcare Life Sciences as Product Code 17-5113-01 are used. These beads are composed of a highly cross-linked, chemically stable, rigid agarose core of about 34 microns in diameter. These beads are well suited for placement in a microtiter samples plate, one bead per 40-µm-diameter well. In addition, these beads are specified to bind 6 mg BSA/mL of beads.

Assuming that the volume of the beads in suspension is approximately $(0.0034)^3$ cm$^3$, then 1.0 mL of beads comprises approximately, $2.5 \times 10^7$ beads/mL. The number of molecules can be determined from 6 mg BSA, which is equal to 90 nmoles or equivalently $5.4 \times 10^{16}$ molecules. Then $5.4 \times 10^{16}$ molecules/$2.5 \times 10^7$ beads is equal to $2.16 \times 10^9$ molecules/bead. If one-tenth of the sites are occupied by mass tags, then ca. $2 \times 10^9$ sites available/bead. This results in 3.3 femtomoles/bead or equivalently 2.6 picomole/mm$^2$ where the area irradiated is taken as the area of a 40-µm-diameter well.

In other methods according to the present teaching, a biotinylated aptamers, which is commercially available from SomaLogic Inc., Boulder, Colo., and biotinylated peptides, which is commercially available from 21$^{st}$ Century Biochemicals, Marlborough, Mass., beads are used. These beads enable simple construction of a diverse array of targeted analyses. In embodiments comprising biotinylated aptamer beads, for example anti-Beta-2-microglobulin, which is commercially available from SomaLogic, Boulder, Colo. as product number B-3485-28_2, the beads and a biotinylated mass tag are mixed the in ratio of 10:1 (aptamer: mass tag) in 20 mM Tris pH 7.3 buffer, 5 mM EDTA (ethylenediaminetetraacetic acid), 1 M NaCl buffer solution. This mixture is allowed to incubate for 30 min. The incubated beads are then collected by centrifugation and washed three times in the same Tris pH 7.3 buffer in the absence of NaCl. The aptamer-to-peptide ratio is chosen to mimic the relative sensitivity for the target analyte and peptide mass tag in the mass spectrometer. The approximate number of binding sites on a single bead is estimated at $2 \times 10^9$.

In one method according to the present teaching, target analytes are sequestered from biological samples by using analyte specific aptamer reagents bound to beads. The beads also contain a mass-tag for bead identification and to aid in analyte signal averaging. Both the analyte specific affinity aptamers and the bead specific mass tags are non-covalently bound to the bead by a biotin/streptavidin linkage.

Some methods according to the present teaching use a plurality of sets of beads in the microtiter sample plate where each set of beads includes a unique mass tag and a unique bait molecule. In these methods, the mass spectrometer can operate in a multiplex mode of operation where mass spectra measurements can be taken on a plurality of different sets of beads and a computer algorithm is used to process the spectra to produce a ligand binding assay for each of the plurality of sets of beads.

Various computer algorithms can be used to process the mass spectra to perform various types of analysis. Some algorithms sum together all of the mass spectra in which a predetermined mass tag is detected to produce a mass spectrum of the bound molecules. Each given mass tag detected corresponds to a unique bait molecule in these algorithms. Thus, the mass spectra in which the mass tag is detected also include the mass of captured prey molecules. The summed mass spectrum for each mass tag is processed to yield mass and intensity for each mass peak detected. These include mass and intensity of the tag molecule ion, mass and intensity of ions produced by captured prey molecules, and may include ions produced from bait molecules. The ratio of the intensity of ions produced from prey molecules to the intensity of molecular ions from the mass tag may be used to determine the concentration of prey molecules in samples of interest. In some embodiments, this may require calibration of this ratio using molecular standards by techniques commonly used in quantitative applications of mass spectrometry.

EQUIVALENTS

While the Applicant's teaching are described in conjunction with various embodiments, it is not intended that the applicant's teaching be limited to such embodiments. On the contrary, the Applicant's teaching encompass various alternatives, modifications, and equivalents, as will be appreciated by those of skill in the art, which may be made therein without departing from the spirit and scope of the teaching.

What is claimed is:

1. An apparatus for ligand binding assay, the apparatus comprising:
   a) an incubator that incubates a plurality of beads with a sample of interest, wherein each of the plurality of beads comprises a tag of predetermined mass and a bait molecule, the incubation binding by a non-covalent bond the bait molecule to a sample molecule contained in the sample of interest;
   b) a washer that washes the incubated beads so that weakly bound sample molecules are removed while strongly bound sample molecules are retained;
   c) a sample plate comprising a plurality of microwells in a region confined by a gasket configured for loading into a MALDI-TOF mass spectrometer;
   d) a sample plate loader that loads a plurality of the incubated and washed beads into the sample plate, the number of the incubated and washed beads loaded into the sample plate being less than a number of beads that can be spread in a monolayer in the region confined by the gasket, the sample plate loader comprising a vibrator configured to agitate the sample plate such that at least some of the number of the incubated and washed beads loaded onto the sample plate settles into one of the plurality of microwells;
   e) a matrix material applicator that deposits matrix assisted laser desorption ionization (MALDI) matrix material onto a surface of the sample plate so that at least some of the plurality of beads are exposed to the MALDI matrix material and that dries the plurality of beads exposed to the MALDI matrix material such that a rupture of the non-covalent bond releases molecules that are incorporated into MALDI matrix crystals;
   f) a matrix assisted laser desorption ionization time-of-flight (MALDI-TOF) mass spectrometer that receives the loaded sample plate and that performs time-of-flight mass spectrometry on the beads positioned on the sample plate, thereby generating mass spectra, wherein a laser beam generated by the MALDI-TOF mass spectrometer used to generate the mass spectra has a beam diameter that is less than a diameter of a microwell; and
   g) a computer that executes an algorithm using the mass spectra generated by the MALDI-TOF mass spectrometer to produce a ligand binding assay.

2. The apparatus for ligand binding assay of claim 1 wherein the sample plate defines a plurality of wells, each of the plurality of wells being dimensioned so that only one bead can be positioned in each well.

3. The apparatus for ligand binding assay of claim 1 wherein the plurality of beads comprises at least two sets of a plurality of beads, wherein each of the at least two sets comprises a mass tag and a bait molecule that are unique to that set.

4. The apparatus for ligand binding assay of claim 1 wherein each of the plurality of beads comprises immobilized streptavidin.

5. The apparatus for ligand binding assay of claim 4 wherein the mass tag molecules and the bait molecules are biotinylated and are bound to the streptavidin immobilized beads.

6. The apparatus for ligand binding assay of claim 1 wherein the mass tag molecules and the bait molecules covalently attach biotin to at least one of a peptide, protein or a nucleic acid.

7. The apparatus for ligand binding assay of claim 1 wherein at least one of the plurality of beads is nominally 34 μm in diameter.

8. The apparatus for ligand binding assay of claim 1 wherein at least one of the plurality of beads comprises biotinylated aptamers.

9. The apparatus for ligand binding assay of claim 1 wherein at least one of the plurality of beads comprises a biotinylated peptide.

10. The apparatus for ligand binding assay of claim 1 wherein the sample plate comprises a microwell sample plate.

11. The apparatus for ligand binding assay of claim 1 wherein the sample plate loader comprises a vibrator.

12. The apparatus for ligand binding assay of claim 1 further comprising a microcentrifuge that collects the plurality of beads.

13. The apparatus for ligand binding assay of claim 1 wherein the matrix material applicator comprises a sprayer.

14. The apparatus for ligand binding assay of claim 1 wherein the laser is configured to raster the laser beam over a surface of the loaded sample plate with a raster interval, a repetition rate, a scanning speed, and a number of summed laser shots per pixel that produces a pixel-size-to-microwell-diameter ratio such that at least half of a pixel associated with a particular microwell has no significant contribution from an adjacent microwell.

15. The apparatus for ligand binding assay of claim 1 wherein the non-covalent bond comprises a streptavidin-biotin bond.

* * * * *